United States Patent [19]
Misic et al.

[11] Patent Number: 5,196,796
[45] Date of Patent: Mar. 23, 1993

[54] ANATOMICALLY CONFORMAL QUADRATURE MRI SURFACE COIL

[75] Inventors: George J. Misic, Novelty, Ohio; Eric D. Reid, Turtle Creek, Pa.

[73] Assignee: Medrad, Inc., Pittsburgh, Pa.

[21] Appl. No.: 740,920

[22] Filed: Aug. 6, 1991

[51] Int. Cl.$^5$ .............................. G01R 33/20
[52] U.S. Cl. .................................. 324/322
[58] Field of Search ............. 324/300, 307, 309, 312, 324/318, 322; 364/413; 333/26; 128/653.5, 653.2

[56] References Cited

U.S. PATENT DOCUMENTS

| | | | |
|---|---|---|---|
| 4,467,282 | 8/1984 | Siebold | 324/309 |
| 4,707,664 | 11/1987 | Fehn et al. | 324/322 |
| 4,752,736 | 6/1988 | Arakawa et al. | 324/318 |
| 4,816,765 | 3/1989 | Boskamp | 324/318 |
| 4,818,942 | 4/1989 | Rzedzian | 324/312 |
| 4,839,595 | 6/1989 | Boskamp | 324/318 |
| 4,843,549 | 6/1989 | McKinnon | 364/413 |
| 4,918,388 | 4/1990 | Mehdizadeh et al. | 324/322 |
| 4,940,941 | 7/1990 | Rzedzian | 324/312 |
| 4,998,064 | 3/1991 | Fuderer et al. | 324/309 |
| 5,030,915 | 7/1991 | Boskamp et al. | 324/318 |
| 5,075,624 | 12/1991 | Bezjak | 324/318 |
| 5,091,708 | 2/1992 | Bezjak | 333/26 |

Primary Examiner—Michael J. Tokar
Attorney, Agent, or Firm—Keck, Mahin & Cate

[57] ABSTRACT

A quadrature surface probe comprising two individual mirror image coil loops arranged so that the magnetic field vectors of the respective coil loops are substantially perpendicular. An area of overlap between the first and second coil loops is adjusted to minimize the mutual coupling between the individual coils. Also disclosed is the method of manufacturing the quadrature surface probe.

11 Claims, 3 Drawing Sheets

ANATOMICALLY CONFORMAL QUADRATURE MRI SURFACE COIL

FIELD OF THE INVENTION

This invention relates to the art of magnetic resonance imaging, and in particular, is related to a quadrature receiving coil and method of making quadrature receiving coil systems whereby isolation between individual coils of the quadrature arrangement is maintained or adjusted by overlapping a select portion of one coil with a select portion of the other.

BACKGROUND OF THE INVENTION

Magnetic resonance imaging (MRI) is a relatively new technology which can be used to display two-dimensional image slices of the human body on a video screen. The technology offers an advantage over conventional X-ray techniques in that the patient is not exposed to harmful ionizing radiation and the adverse effects therefrom. MRI systems can also be used to observe many different types of atoms and can identify the chemical environment of the atoms.

In operation, a magnetic resonance imaging system uses a strong main magnetic field to selectively orient atoms having an odd number of protons in their nuclei. A second magnetic field oscillating at a radio frequency rate, usually applied at right angles to the main field, is then used to flip these nuclei into an inverted state. When the applied magnetic field is subsequently removed, the nuclei relax from their inverted state, and in doing so, radiate energy in the form of weak but detectable electromagnetic waves. The resulting signals are then received and used by the MRI system to generate a two-dimensional display of a specimen's composition.

To accomplish all this, magnetic resonance imaging systems generally comprise a main magnetic field generator, a radio frequency excitation means, control/display circuitry, and a magnetic resonance receiving probe. The main magnetic field generator provides a main magnetic field along a Z-axis for the purpose of aligning individual atoms. The radio frequency (RF) excitation means selectively excites the nuclei of these atoms, and subsequently allows the nuclei to relax. The resulting electromagnetic signal produced by the relaxing nuclei is then received by the receiving probe and processed by the control/display circuitry to produce an image representative of the specimen's composition.

The received electromagnetic signals are in the form of a circularly polarized or rotating magnetic field, having an axis of rotation aligned with the main magnetic field of the MRI system. By using a receiving probe capable of constructively adding the two perpendicular components of the rotating magnetic field, a stronger signal can be extracted by the MRI system. Receiving probes of this type which measure two perpendicular components of a magnetic resonance signal are well known in the art and are commonly referred to as quadrature probes or quadrature coils.

For an ideal quadrature probe structure, isolation between the individual coils must be maintained, as well as the perpendicular relationship between their respective field vectors. Maintaining isolation along with a perpendicular relationship, tends to optimize the signal-to-noise ratio of the receiving probe and thereby improves the overall signal-to-noise ratio of the MRI system.

Quadrature probes, in the past, have been devised from a variety of individual coil configurations, including generally cylindrical shapes as well as planar structures. Regardless of which configuration is used, it has always been a difficult undertaking to maintain the isolation between quadrature coils while at the same time, maintaining the perpendicular relationship between their magnetic vectors.

One such attempt at providing maximized coil isolation contemporaneously with maintenance of a perpendicular magnetic relationship, is disclosed in Arakawa U.S. Pat. No. 4,752,736. See also, Siebold U.S. Pat. No. 4,467,282, one of the early quadrature coil patents disclosing a uniform symmetrical volume coil. In particular, U.S. Pat. No. 4,752,736 discloses a rather complex coil structure utilizing a series of breaks, conductive bridges, and capacitive elements to provide isolation between the individual coils of the system. This complex coil configuration is of the volume type and, therefore, completely surrounds the specimen or patient being analyzed.

Another quadrature coil arrangement is disclosed in Fehn U.S. Pat. No. 4,707,664. According to the patent, a surface coil configuration is disclosed and consists of two separate coils. Each coil is rigidly mounted to a separate quasi-cylindrical substrate. One substrate and its respective coil is circumferentially surrounded by the other substrate and coil such that the inner substrate is retained. In addition to being retained, the inner substrate can be adjusted to assume any angular orientation with respect to the other substrate. In this way, the angle between the individual coils can be adjusted to maximize isolation, and thereby, increase the overall signal-to-noise ratio. If the isolation must be adjusted further, a series of isolating capacitive couplings can be connected across predetermined portions of the surface coils.

Planar quadrature coil systems are disclosed in Boskamp U.S. Pat. No. 4,839,595 and Mehdizadeh et al. U.S. Pat. No. 4,918,388. These coil systems comprise two coil loops mounted side-by-side (Boskamp) or on top of each other (Mehdizadeh) in a planar dielectric sheet.

SUMMARY OF THE INVENTION

A primary object of the present invention is to provide a quadrature surface coil which utilizes only two independent coils rather than three or more dependant coils.

Another object of the present invention is to provide a quadrature surface coil which specifically enhances the signal reception over a region of interest while deliberately excluding signals from areas outside of the region of interest It is yet another object of the present invention to provide a quadrature surface coil having two independent coils with mirror symmetry and equal sensitivity to the subject anatomy, thus providing nearly the full theoretical gain (41.4%) in signal-to-noise ratio from the quadrature coil.

It is a further object of the present invention to provide a means for minimizing the mutual coupling between the two independent coils of the quadrature surface probe by selectively varying a region of overlap between the two coils.

An additional object of the present invention is to provide a quadrature surface probe and method of adjusting the quadrature probe such that adjustments to the shape of the independent coils by way of bending or other means, provides a way of adjusting the magnetic vectors of the coils to achieve a 90° relationship therebetween.

An even further object of the present invention is to provide a quadrature surface probe wherein the combination of mutual isolation and a perpendicular magnetic relationship is achieved by intermittently adjusting a region of overlap between the coils and adjusting the coil shapes, respectively.

It is an additional object of the present invention to provide a quadrature surface probe that conforms to the anatomical shape of the specimen or patient being analyzed.

It is a still further object of the present invention to provide a quadrature surface probe for use in the art of magnetic resonance imaging wherein a patient or object being analyzed, is not completely surrounded by the probe assembly, but instead typically encircled by less than 180°.

Another object of the present invention is to provide a quadrature surface probe that is independent of planar symmetry and relies solely upon mirror symmetry.

Yet another object of the present invention is to provide a method for manufacturing such a probe.

Still another object of the present invention is to provide a quadrature surface probe in which the isolation of independent coils is readily adjustable.

In accordance with the present invention, a quadrature surface probe is provided for optimal interception of the radio frequency oscillating magnetic fields generated by a human subject or other object during Magnetic Resonance Imaging (MRI) or Magnetic Resonance Spectroscopy (MRS). The surface probe comprises two loops of simple or irregular shape having mirror symmetry about a plane parallel to the axis of the main magnetic field of the MR system; the loops also surround the object or region of interest in a partial volume manner, typically wrapping around less than 180° of the object's perimeter. The two loops are arranged in such a manner that the net magnetic vector of one loop is generally displaced from the net magnetic vector of the other loop by an angle of about 90°, the optimal angle for these vectors being exactly 90°. For human subjects, in the region of the cervical spine or similar area, this will cause the vectors to be positioned at approximately 45° and 135° in a conventional XYZ coordinate system, where the Z axis is parallel to the main static magnetic field. Additionally, the loops are so shaped and so positioned that the mutual inductance, and therefore the majority of the coupling between the two loops, is minimized. This is accomplished by overlapping a critical portion of the area enclosed by the loops, causing a sharing of the proper amount of inphase flux to exactly cancel the balance of the outphase shared flux. This, in turn, results in no net shared flux and, therefore, a net mutual inductance of zero.

Furthermore, by making the two independent coil loops mirror images of one another, the full theoretical gain of 41.4% may be more closely approaches as a result of the signal at the output of the coil loops being equal in magnitude.

The aforementioned and other objects, features, and advantages of the present invention will become apparent from the following description of the preferred embodiment, as well as from the associated drawings, all of which merely illustrate the inventive concept, and are in no way intended, nor should they be construed, to limit the scope of the instant invention.

DESCRIPTION OF THE PREFERRED EMBODIMENT

A specific embodiment of the invention, presented for purposes of illustration, is hereinafter described in the form of a cervical spine coil.

Figures 1A, 1B:
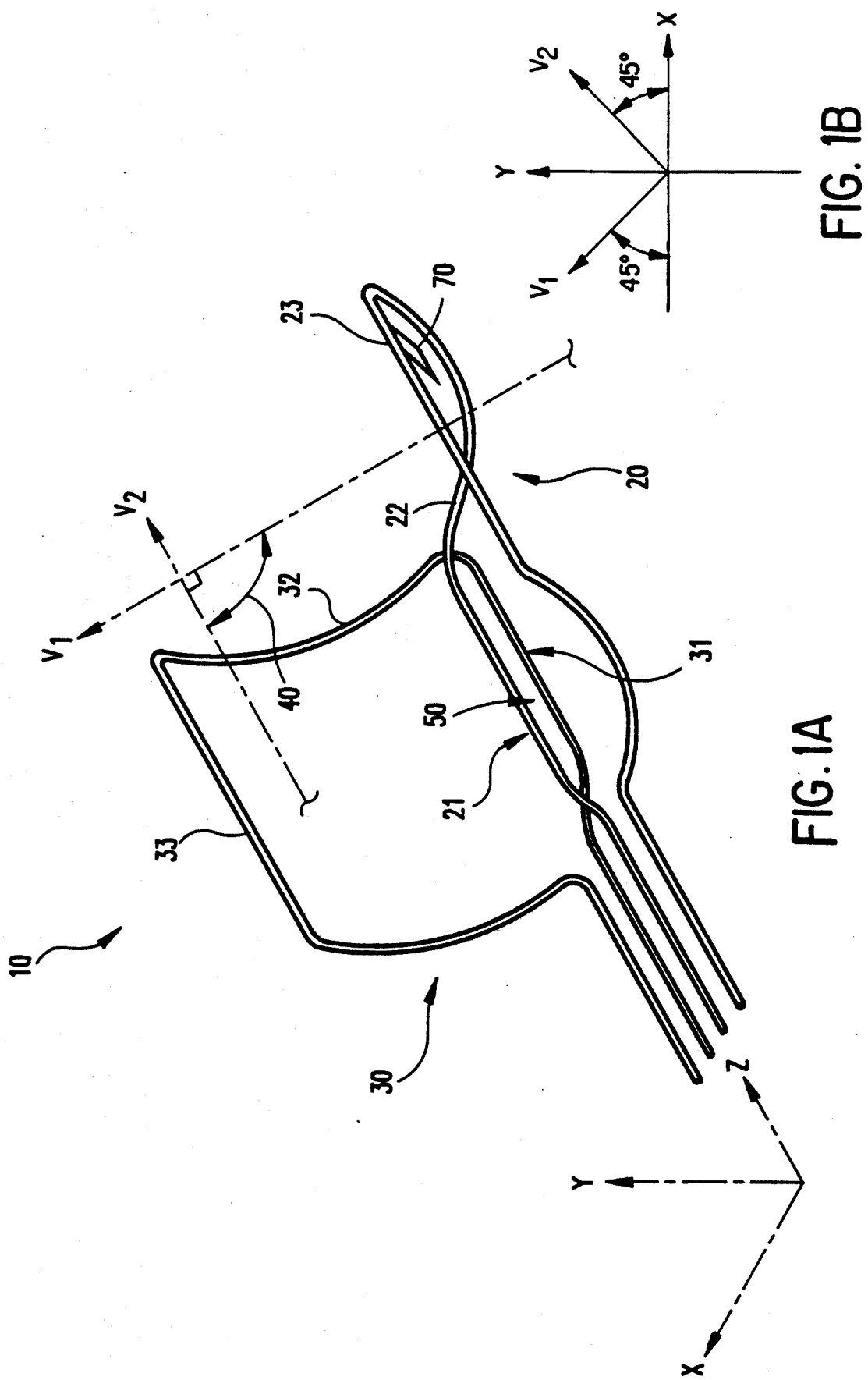
FIG. 1A is a perspective view of two coil loops forming the basis of the quadrature surface coil in accordance with the present invention.
FIG. 1B is a graphical illustration of the relative orientations of the magnetic field vectors of the respective coil loops shown in FIG. 1A.

Referring first to FIG. 1A, the quadrature coil is shown generally at 10 comprising two coil loops 20 and 30, which are mirror image duplicates of one another. That is, coil loops 20 and 30 are the same size and are shaped as mirror reflections of each other. Each of the coil loops 20 and 30 comprises three conductor sections 21, 22, 23, and 31, 32, 33, respectively.

The coil loops 20 and 30 are oriented with respect to each other so that the net magnetic vector $V_1$ from loop 20 is perpendicular to the net magnetic vector $V_2$ from loop 30. It is preferred that the angle 40 between $V_1$ and $V_2$ be 90° or as close to 90° as possible; with 90° being the optimal angle. Consequently, as shown in FIG. 1B, this means that the angle between both vectors and the X-axis is 45°.

The coil loops 20 and 30 are shaped and positioned so that the mutual inductance is minimized. Therefore, the loops are substantially electrically isolated from one another. This is achieved by overlapping an area enclosed by the loops; moving the loops toward or away from each other. Overlapping adjustments are made while maintaining the angular tilt of each loop fixed in the aforementioned orientation. However, after overlapping adjustments are made, the relative tilt of the loops may be further adjusted.

Figure 2:
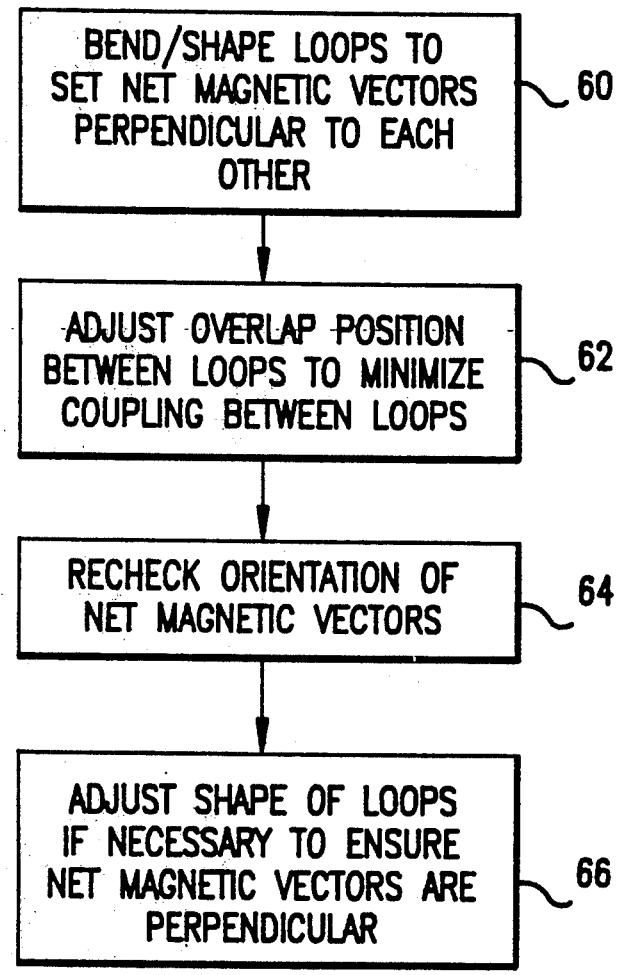
FIG. 2 is a flow chart illustrating the steps of constructing the quadrature surface probe in accordance with the present invention.

The steps of constructing the coil system according to the present invention is shown in FIG. 2. The quadrature coil 10 is constructed by first, in step 60, bending two coil loops 20 and 30 and adjusting the curvature and shape of the loops to develop exactly a 90° angle between the net magnetic field vectors created by each coil loop. Next, in step 62, the isolation between the coil loops is checked and any repositioning of the coil loops is made to adjust the overlap for total isolation. The relative orientation of the net magnetic vectors $V_1$ and $V_2$ is checked again in step 64. Finally, if necessary, the curvature or shape of each coil is adjusted in step 66 to ensure the 90° angle between the respective magnetic vectors. In most cases, it is sufficient to adjust the curvature and shape of the coils to get the 90° vector angle, so long as the overlap of the coil loops is within a permissible range.

The process of constructing the loops is an iterative process. The vector position, flux coverage and isolation is a function of the coil shapes, positions and overlap. Consequently, steps 62-66 may be repeated several times to achieve desired flux orientation. In practice, each coil loop is resonated and matched to 100 Ohms. A network analyzer is used to measure the coupling between the coils according to an S21 measurement with one coil loop connected to Port 1 of the analyzer and the other coil loop connected to Port 2. The magnitude of coupling is minimized by adjusting the coils for the minimum value of S21. With simpler instruments, a signal generator may be applied to one coil loop and an oscilloscope to another. The coils are adjusted to minimize the signal level on the oscilloscope. To measure the direction of flux, a Faraday-shielded sampling loop is used such that the flux will be normal to the position where the sampling loop provides the greatest signal magnitude.

The geometry of the overlap between coil loops 20 and 30 is fixed for production, having been determined during the development stage. To adjust isolation, either the coil conductor position is moved slightly, or a copper tab 70 may be added to one loop to slightly alter the current path.

Figure 3:
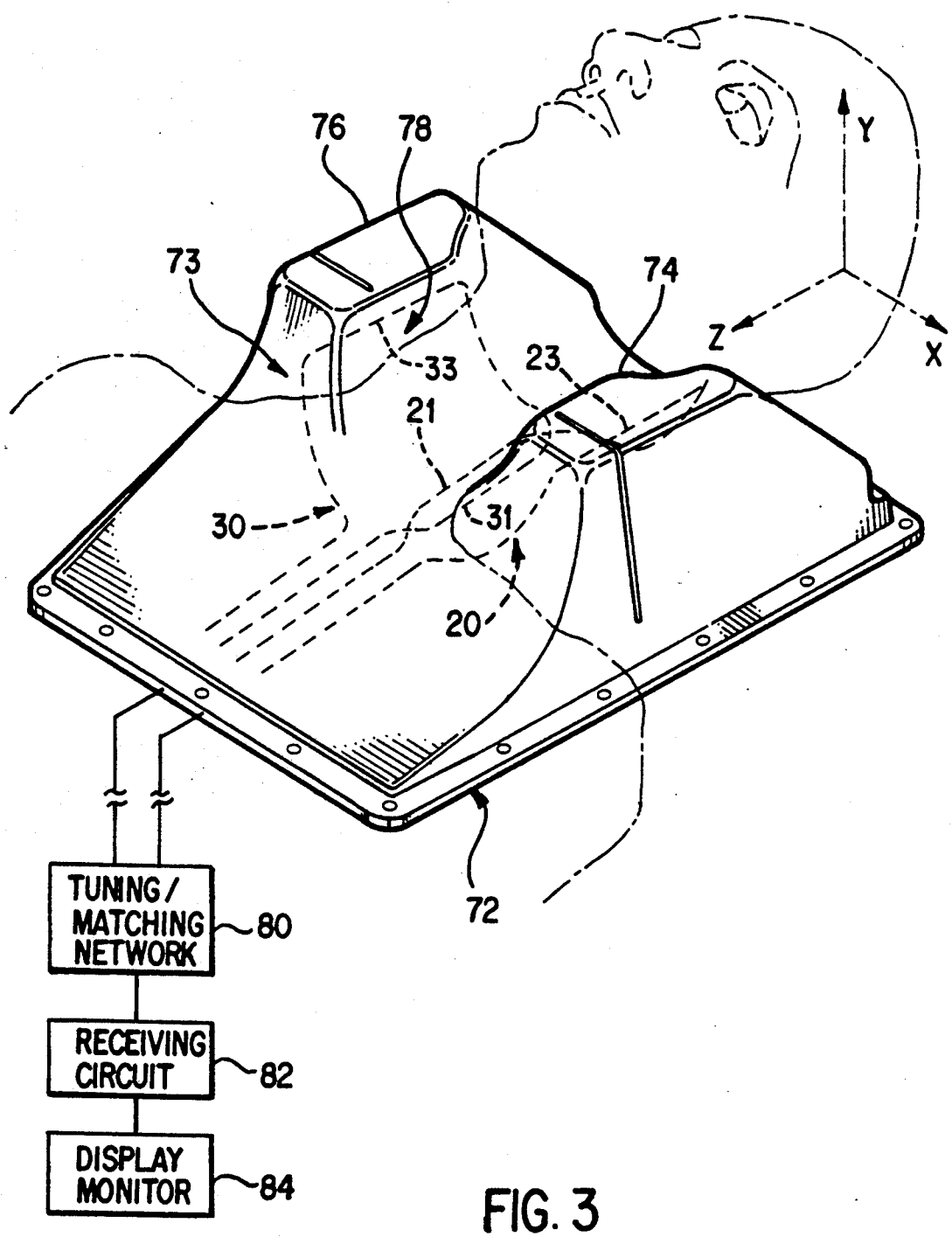
FIG. 3 is a perspective view of the quadrature surface coil mounted in a plastic housing and connected to receiving and displaying circuitry as part of a magnetic resonance imaging system.

FIG. 3 illustrates a view from above of the housing with the coil loops 20 and 30 mounted therein. The housing 72 comprises a gradual upward sloping surface 73 leading to two identical saddle-shaped sides 74 and 76. The sides 74 and 76 are joined by an elliptical surface portion 78, therebetween, designed to support the neck of a patient. Portions 21 and 31 of the coil loops 20 and 30 extend side-by-side along the bottom of the housing 70 and portions 23 and 33 follow the elliptical surface portion 78 along respective ones of the sides 74 and 76. The shape of the sides 74 and 76 of the housing is prefabricated according to a predetermined "rough" shape and orientation of the coil loops 20 and 30.

As is well known in the art, the coil system is connected to an electronic network 80 which includes tuning and impedance matching components. The network may be contained within the housing 72 or external thereto and is connected to the coil loops 20 and 30 through conventional connections. The electronic tuning and matching network 80 is connected to a receiving circuit 82, which among other things, amplifies the output of the network 80 for displaying the image data on the display monitor 84.

As is well known in the art, the quadrature surface probe 10 is used in the presence of a static magnetic field and in conjunction with an excitation coil and an RF generator to deliver excitation field to the patient.

It is envisioned that an adjustment mechanism may be provided in the housing for moving the coil loops to compensate for small irregularities, unit-to-unit, created by real-world tolerances.

The foregoing description is intended by way of example only and is not intended to limit the present invention in any way except as set forth in the following claims.

We claim:

1. A magnetic resonance quadrature surface probe for detecting magnetic resonance signals comprising:
   a first coil loop having a first net magnetic field vector;
   a second coil loop having a second net magnetic field vector;
   said first and second coil loops being shaped to be mirror images of each other and oriented relative to each other so that said first and second net magnetic field vectors are substantially perpendicular to one another.

2. The probe of claim 1, wherein a region of overlap between the first and second coil loops is provided for obtaining a desired level of isolation between the first coil loop and the second coil loop.

3. The probe of claim and further comprising a housing for enclosing said first and second coil loops, said housing being shaped to conform with the anatomical configuration of the human cervical spine.

4. A magnetic resonance quadrature surface probe for detecting magnetic resonance signals, said quadrature surface probe comprising:
   a first non-planar coil loop having a first net magnetic field vector;
   a second non-planar coil loop having a second net magnetic field vector;
   said first and second coil loops being shaped so as to be mirror images of each other and oriented so that the first and second net magnetic field vectors are substantially perpendicular to each other; and
   a region of overlap being provided between the first coil loop and the second coil loop.

5. The magnetic resonance system of claim 4, wherein said first and second coil loops are bent and positioned with respect to each other so as to form a cradle into which the body part to be imaged is received.

6. The magnetic resonance system of claim 4, and further comprising a conductive strip attached to one of said first and second coil loops to alter the current path therein for adjusting isolation between the first and second coil loops.

7. A method for constructing a quadrature MRI surface probe comprising the steps of:
   bending first and second electrically conductive loops into non-planar orientations whereby the first and second loops are mirror images of one another;
   adjusting the orientation, curvature and shape of the first and second loops so that a first net magnetic field vector of the first loop is substantially perpendicular to a second magnetic field vector of the second loop;
   determining the degree of isolation between the first and second loops; and
   adjusting an overlap between the first and second loops to obtain a desired degree of isolation.

8. The method of claim 7, and further comprising the step of repeating the steps of adjusting curvature and adjusting the overlap to minimize isolation and ensure the perpendicular relationship of the magnetic vectors of the first and second loops.

9. The magnetic resonance system of claim 7, and further comprising the step of attaching a conductive strip to one of said first and second loops to adjust the isolation therebetween.

10. A magnetic resonance imaging system comprising:
    means for generating a static magnetic field about a patient;
    means for generating an oscillating magnetic field and applying said oscillating field to a region of interest of a patient; and
    a quadrature surface probe for detecting magnetic resonance signals from said region of interest, said probe comprising:
    a first coil loop having a first net magnetic field vector;

a second coil loop having a second net magnetic field vector;

said first and second coil loops being shaped to be mirror images of each other and oriented relative to each other so that said first and second net magnetic field vectors are substantially perpendicular to one another;

receiving circuitry for amplifying the detected magnetic resonance signals; and display means for displaying a magnetic resonance image of said region of interest on the basis of said detected magnetic resonance signals.

11. The system of claim 10, wherein a region of overlap between the first and second coil loops of said quadrature surface probe is provided for obtaining a desired level of isolation between the first coil loop and the second coil loop.

* * * * *